United States Patent
Meah

(12) 
(10) Patent No.: US 6,257,238 B1
(45) Date of Patent: Jul. 10, 2001

(54) BITE BLOCK FOR UPPER GASTROINTESTINAL ENDOSCOPY WITH TONGUE DEPRESSOR

(76) Inventor: Nizam M. Meah, 236 Plum Cir., Lake Jackson, TX (US) 77566

( * ) Notice: Subject to any disclaimer, the term of this patent is extended or adjusted under 35 U.S.C. 154(b) by 0 days.

(21) Appl. No.: 09/578,422

(22) Filed: May 25, 2000

(51) Int. Cl.[7] ..................................................... A61C 5/14
(52) U.S. Cl. ...................... 128/859; 128/861; 128/200.26
(58) Field of Search ..................................... 128/846, 848, 128/859–862, 200.26; 602/902; 604/174

(56) References Cited

U.S. PATENT DOCUMENTS

| | | | | |
|---|---|---|---|---|
| 4,270,531 | * | 6/1981 | Blachly | 128/861 |
| 4,495,945 | * | 1/1985 | Liegner | 128/200.26 |
| 5,174,284 | * | 12/1992 | Jackson | 128/859 |
| 5,413,095 | * | 5/1995 | Weaver | 128/200.26 |
| 5,533,523 | * | 7/1996 | Bass | 128/861 |
| 5,590,643 | * | 1/1997 | Flam | 128/860 |
| 5,682,904 | * | 11/1997 | Stinnett | 128/861 |

* cited by examiner

*Primary Examiner*—Michael A. Brown
(74) *Attorney, Agent, or Firm*—John R. Merkling

(57) ABSTRACT

A bite block for upper gastrointestinal endoscopy having a tubular body with a proximal end and a distal end and defining a channel open at the proximal and distal ends, a shield connected to the tubular body at the proximal end, and a tongue depressor connected to the tubular body at the distal end. The tongue depressor comprises a plate connected to a bottom side of the distal end of the tubular body and is curved downwardly. The bite block has a chamber open to the channel in the bite block. A viscous bio-compatible lubricant in said chamber can contact and coat the end of an endoscope or other instrument when the instrument is inserted through the bite block. A removable tab can be pulled away from an opening into the chamber to expose the lubricant after the bite block has been placed in a patient's mouth. A lumen extends from the proximal end to the distal end of the tubular body, through the wall of the tubular body. An additional cannula or needle may be inserted through the lumen past the bite block and into the back of the throat, while isolating the additional needle from the endoscope.

15 Claims, 3 Drawing Sheets

BITE BLOCK FOR UPPER GASTROINTESTINAL ENDOSCOPY WITH TONGUE DEPRESSOR

FIELD OF THE INVENTION

The present invention relates to apparatus for use in conducting gastrointestinal endoscopy and particularly to a bite block.

BACKGROUND OF THE INVENTION

Upper gastrointestinal endoscopy (also known as upper endoscopy, upper GI endoscopy, esophago-gastro-duodenoscopy [EGD], or panendoscopy) is a procedure employed by a physician to examine the lining of the upper part of a patient's gastrointestinal tract. Upper gastrointestinal endoscopy is usually used to investigate symptoms of persistent upper abdominal pain, nausea, vomiting, difficulty in swallowing, or bleeding in the upper gastrointestinal tract.

To perform gastrointestinal endoscopy, a physician inserts a thin, flexible tube with a lens, fiber optic view transmission path and light source (an endoscope) into the patient's gastrointestinal tract through the patient's mouth. The physician may be able to observe inflammation, ulcers, or tumors of the esophagus, stomach or duodenum. In addition, certain conditions may be treated. By inserting a variety of instruments through a lumen in the endoscope, a physician may stretch narrowed areas, remove polyps, retrieve swallowed objects, or treat bleeding.

A patient prepares for an endoscopy by fasting to clear the gastrointestinal tract. The physician may spray a local anesthetic into the patient's throat before the test and intravenous or other medication may be given to help the patient relax. A bite block may be placed in the patient's mouth to keep the patient's jaws open. A prior art bite block 10 is illustrated in FIG. 1. The bite block 10 comprises a tubular body 12, having a proximal end 14 and a distal end 16. A channel 18 extends through the tubular body 12. The endoscope (not shown) or other instruments may be inserted through this channel into the patient's throat. A shield 20 at the proximal end 14 of the bite block 10 has left and right lateral wings 22, 24 respectively, which shield a part of the patient's lips and extend onto the patient's left and right cheeks. Each wing 22, 24 has a tab or clip 26, 28. An elastic band (not shown) may be attached to the clips 26, 28 and passed around the patient's head to secure the bite block. In the usual case, the endoscope or other instrument is then partially coated with a sterile, bio-compatible lubricant, for example, petroleum jelly, to aide in inserting the endoscope into the throat.

Although a upper gastrointestinal endoscopy is a widely used procedure, it is sometimes difficult to insert the endoscope. Because of the medication given to the patient to relax the patient's muscles, the patient's tongue will sometimes relax into the back of the patient's mouth, sometimes covering or entering the channel 18 of the bite block 10 and blocking the patient's throat. Moreover, manually applying lubricant to the exterior of an endoscope may present difficulties in handling and sterilizing the endoscope or the lubricant. Finally, it is sometimes desirable to insert and additional cannula or device past the bite block and into the back of the throat, while isolating the additional cannula or device (e.g., a needle, suction tube, oxygen supply line or other such device) from the endoscope. There remains a need, therefore, for additional improvements in the instrumentation used for gastrointestinal endoscopy.

SUMMARY OF THE INVENTION

I have invented a bite block for upper gastrointestinal endoscopy having a tubular body with a proximal end and a distal end and defining a channel open at the proximal and distal ends, a shield connected to the tubular body at the proximal end, and a tongue depressor connected to the tubular body at the distal end. The tongue depressor comprises a plate connected to a bottom side of the distal end of the tubular body and is curved downwardly.

In another aspect of my invention, the bite block has a chamber open to the channel in the bite block. A viscous bio-compatible lubricant in said chamber can contact and coat the end of an endoscope or other instrument when the instrument is inserted through the bite block. A removable tab can be pulled away from an opening into the chamber to expose the lubricant after the bite block has been placed in a patient's mouth.

In yet another aspect of my invention, a lumen extends from the proximal end to the distal end of the tubular body, through the wall of the tubular body. An additional cannula, needle or other device may be inserted through the lumen past the bite block and into the back of the throat, while isolating the additional device from the endoscope. The lumen may also be used to deliver oxygen during the endoscopic procedure. This can be particularly helpful for a patient who does not breathe through the nose. Additional oxygen may relieve discomfort caused by the presence of the bite block and endoscope in the mouth and throat of the patient.

These and other features and advantages of the present invention will be apparent to one skilled in the art from the following detailed description, connection with the accompanying drawings.

Detailed Description

Figure 1:
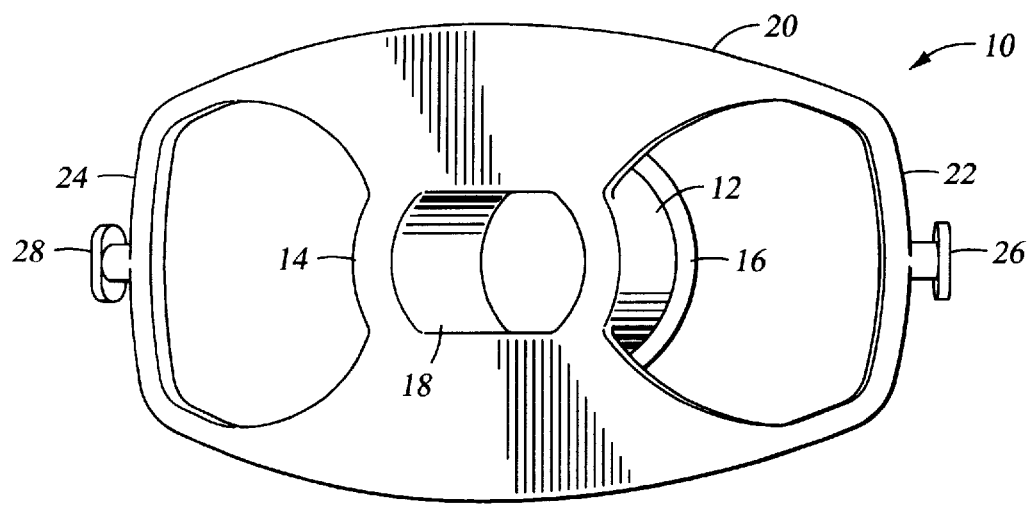
FIG. 1 is a front perspective view of a bite block according to the prior art.
Figure 2:
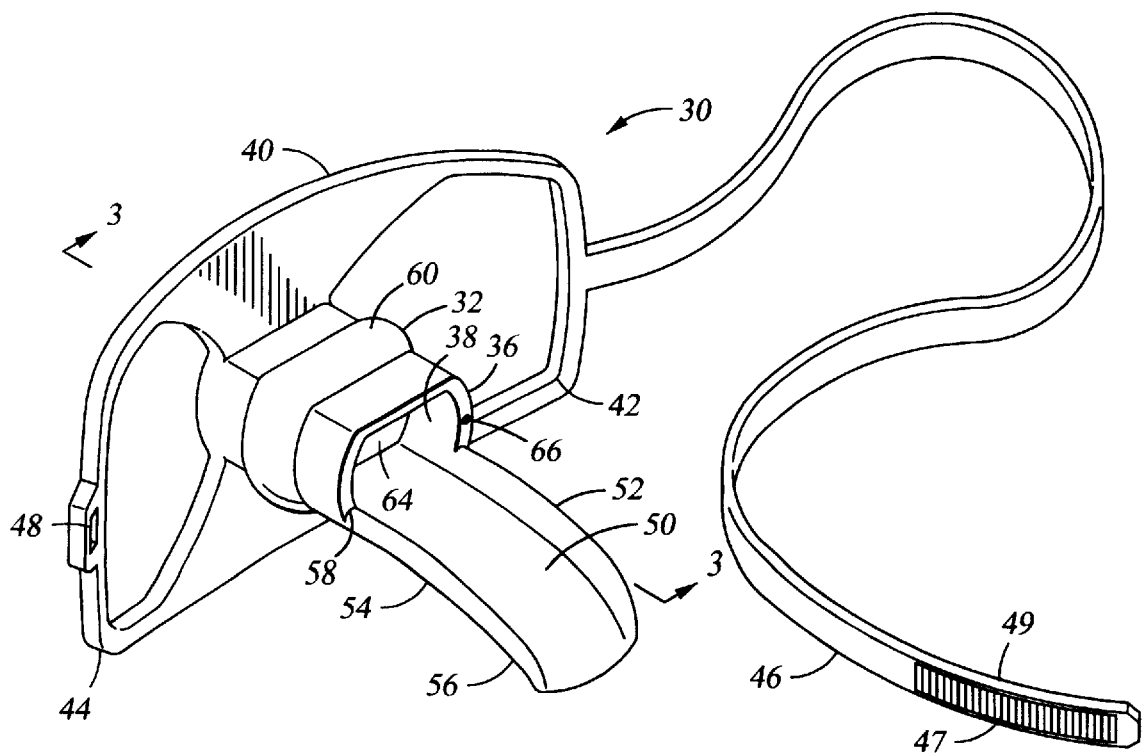
FIG. 2 is a rear perspective view of a bite block according to the present invention.
Figure 3:
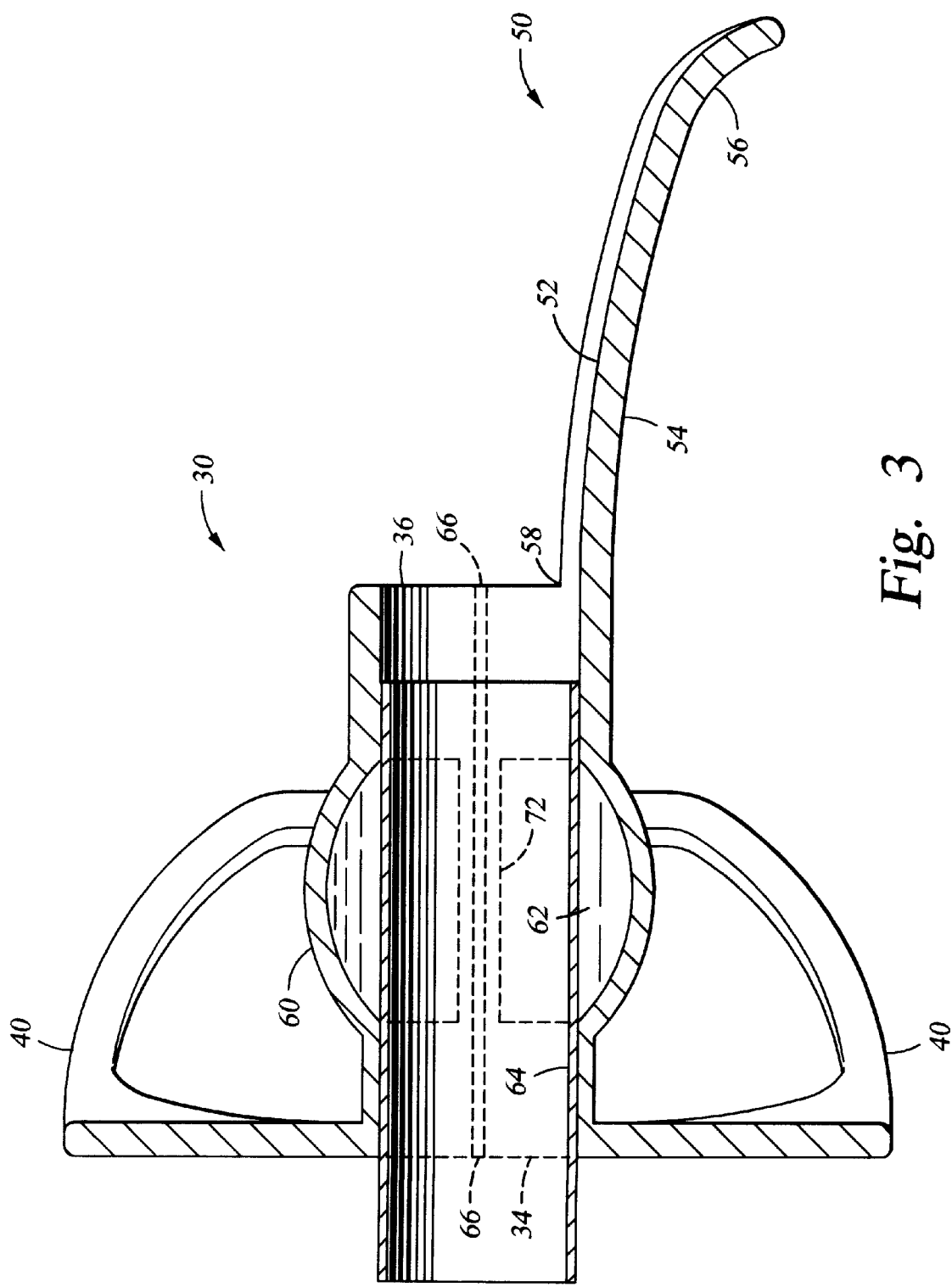
FIG. 3 is a through section of the bite block of FIG. 2, taken along line 3—3.

I will now describe my invention with reference to the accompanying drawings, wherein like numerals are used to describe like parts in the various views. In FIG. 2, a bite block 30 according to my invention is illustrated in perspective view. In common with the prior art, the bite block 30 comprises a tubular body 32, having a proximal end 34 and a distal end 36. A channel 38 extends through the tubular body 32. An endoscope 70 (FIG. 4) or other instruments may be inserted through this channel into the patient's throat. A shield 40 at the proximal end 34 of the bite block 30 has left and right lateral wings 42, 44 respectively, which shield a part of the patient's lips and extend onto the patient's left and right cheeks. Each wing 42, 44 may have a tab or clip, like the tabs 26, 28 shown in FIG. 1. An elastic band (not shown) may be attached to the tabs and passed around the patient's head to secure the bite block. Preferably, however, I have provided a attachment feature for the bite block of my invention comprising a strip 46 attached to a wing 42 of the bite block. The strip 46 is long enough to extend around a patient's head and has a set of teeth or indentations 47 at a free end 49. The free end 49 is inserted into a female socket 48 mounted on the other wing 44. The female socket has a tooth or latch to engage the indentations on the strip 46 in the manner of a cable tie. The strip can, therefore, be inserted easily into the socket 48, but cannot be removed without considerable force. Since the bite block is intended to be used only once, it is preferred that the strip 46 be cut to remove the bite block.

The bite block 30 of my invention also includes a tongue depressor 50 connected to the distal end 36 of the bite block 30. The tongue depressor 50 has an upper surface 52 which is slightly concave from a right side to a left side. This concave surface 52 helps to guide the endoscope during insertion into the throat. There is also a lower surface 54 which is slightly convex from side to side, congruent with the upper surface 52. The tongue depressor curves downwardly in a gentle arc 56 from its connection to the tubular body 32 at a lower edge 58 of the distal end 36 of the tubular body 32 and the upper surface 52 may therefor be described as having a convex curve from a proximal end to a distal end. Similarly, the lower surface 54 has a corresponding concave curve from the proximal end to the distal end.

Figure 4:
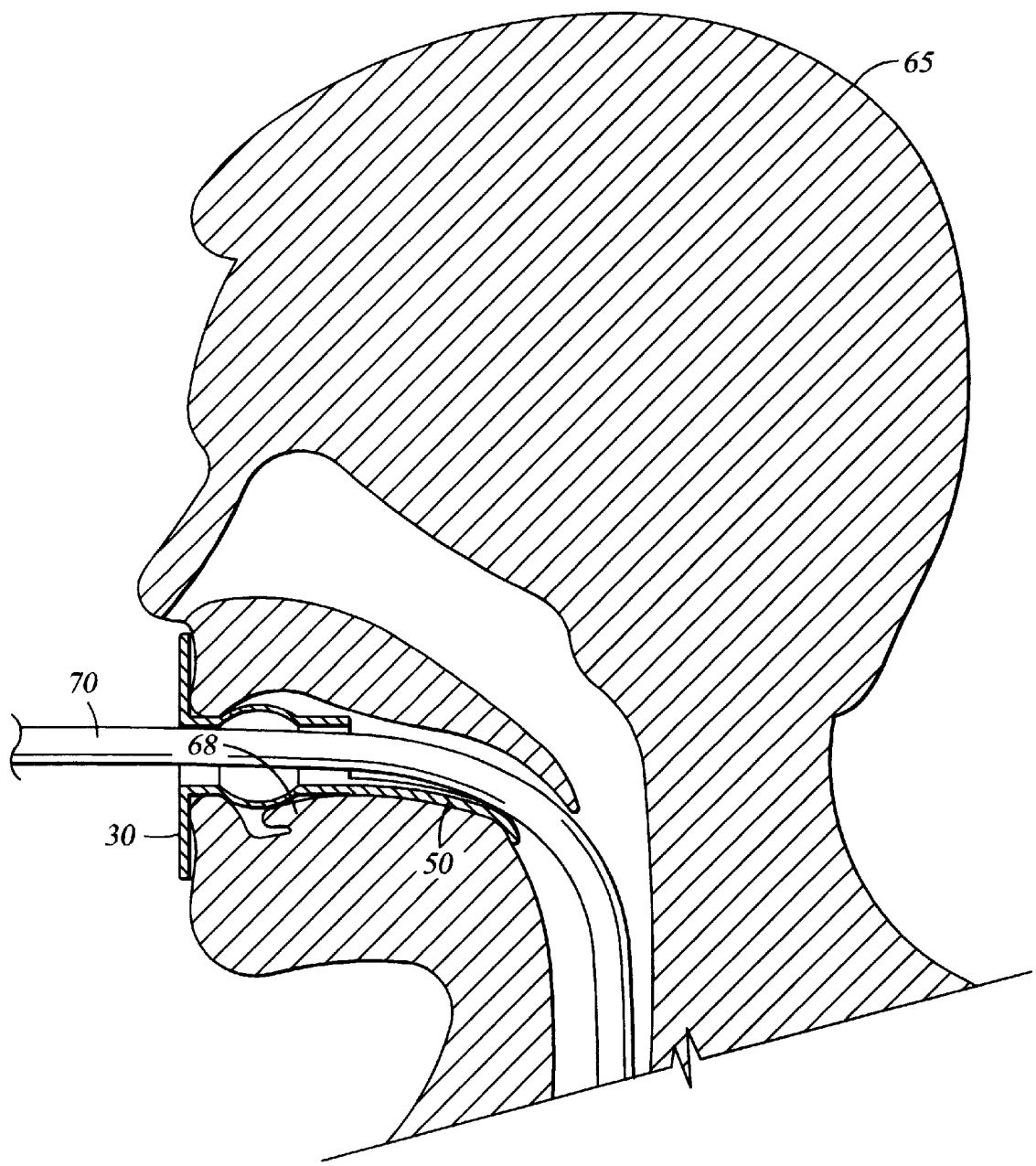
FIG. 4 is a representation of a patient using the bite block of the present invention.

The tongue depressor 50 presses against the tongue 68 of a patient 66, as illustrated in FIG. 4, when the bite block 30 is inserted into the mouth of a patient. Under the influence of sedation, anesthesia or muscle relaxants, a patient's tongue may fall into the rear of the mouth and block access to the gastrointestinal tract. The tongue depressor 50 prevents this from occurring and provides the physician with unobstructed access to insert the endoscope 70.

Heretofore when the endoscope 70 was inserted into the gastrointestinal tract of a patient, the endoscope was manually coated with a bio-compatible lubricant before being inserted into the bite block 10. In the bite block 30 of my invention, a chamber 60 on the tubular body 32 is filled with a bio-compatible lubricant 62. The chamber 60 opens into the channel 38. Preferably, the chamber substantially circumscribes the tubular body. A removable pull tab or sleeve 64 usually closes the chamber 60 and covers the lubricant 62. After placing the bite block 30 in the patient's mouth but before inserting the endoscope 70, a physician would remove the sleeve 64, thereby exposing the lubricant 62 to the channel 38. As the physician advances the endoscope 70 into the channel 38 in the bite block 30, he or she would pass the end or side of the endoscope 70 into the lubricant 62. The endoscope can thereby be lubricated in the process of insertion into the gastrointestinal tract of the patient. This eliminates the potentially messy procedure of coating the endoscope before the endoscope in passed into the patient's mouth.

After the endoscope has been placed in the patient's gastrointestinal tract, it may be desirable to insert another catheter or other instrument without disturbing or damaging the endoscope. For example, it may be desirable to deliver oxygen, medication, sedation or anesthetic through a needle or cannula into the back of the mouth. In the bite block 30 of my invention, a lumen 66 extends from the proximal end 34 to the distal end 36 of the tubular body 32. Preferably, the lumen 66 passes through the wall of the tubular body, parallel to the channel 38, but separated from the channel. If the chamber 60 for lubricant is substantially circumferential of the tubular body 32, as described above, a passage 72 may be provided through the chamber 60 such that the lumen extends without interruption from the proximal end to the distal end of the tubular body. This may be accomplished, for example, by interrupting the chamber 60 such that it is not completely circumferential or by inserting a tube into the lumen 66 from the proximal to the distal end thereof. The lumen is preferably on the left side of the bite block 30, adjacent the tongue depressor 50. Patients are most frequently positioned on their left side for upper gastrointestinal endoscopy. The lumen 66 permits the physician to insert a needle, for example, through the lumen 66 and reach the back of the patient's mouth without disturbing or damaging the endoscope 70 or other instrument which may already be inserted through the channel 38. Placing the lumen 66 down and left on the tubular body 32 usually means that the needle or device will be at lowest part of the patient's mouth. The lumen may also be used to introduce a suction device to the back of the patient's mouth to remove saliva or other fluids, which would accumulate at the lowest part of the mouth, consistent with the position of the patient.

Although I have now described my invention in connection with my preferred embodiment, those skilled in the art will recognize that my invention may take other forms without departing from the spirit or teachings thereof. The foregoing description is intended, therefore, to be illustrative and not restrictive, and the scope of my invention is to be defined by the following claims.

What is claimed is:

1. A bite block for upper gastrointestinal endoscopy comprising a tubular body having a proximal end and a distal end and defining a channel open at said proximal and distal ends, a chamber open to said channel and a viscous biocompatible lubricant in said chamber, a shield connected to said tubular body at said proximal end, and a tongue depressor connected to said tubular body at said distal end.

2. The bite block of claim 1 wherein said tongue depressor comprises a plate connected to a bottom side of said distal end of said tubular body.

3. The bite block of claim 2 wherein said plate of said tongue depressor is curved downwardly from a proximal end to a distal end.

4. The bite block of claim 3 further comprising a lumen extending from said proximal end to said distal end of said tubular body.

5. The bite block of claim 4 wherein said tubular body comprises a generally cylindrical wall and said lumen extends through said wall.

6. The bite block of claim 1 wherein said tongue depressor is curved downwardly.

7. The bite block of claim 6 further comprising a lumen extending from said proximal end to said distal end of said tubular body, said lumen being generally parallel to said channel and separated therefrom.

8. The bite block of claim 7 wherein said tubular body comprises a generally cylindrical wall and said lumen extends through said wall.

9. The bite block of claim 1 further comprising a lumen extending from said proximal end to said distal end of said tubular body, said lumen lying generally parallel to said channel and separated therefrom.

10. The bite block of claim 9 wherein said tubular body comprises a generally cylindrical wall and said lumen extends through said wall.

11. The bite block of claim 9 wherein said lumen interrupts said chamber.

12. A bite block for upper gastrointestinal endoscopy comprising
- a tubular body having a proximal end and a distal end and defining a channel open at said proximal and distal ends,
- a shield connected to said tubular body at said proximal end, and
- a chamber open to said channel and a viscous biocompatible lubricant in said chamber.

13. The bite block of claim 12 further comprising a removable covering between said chamber and said channel.

14. The bite block of claim 12 further comprising a lumen extending from said proximal end to said distal end of said tubular body.

15. The bite block of claim 14 wherein said tubular body comprises a generally cylindrical wall and said lumen extends through said wall.

\* \* \* \* \*